United States Patent [19]

Lee

[11] Patent Number: 4,632,904
[45] Date of Patent: Dec. 30, 1986

[54] IMMOBILIZED ENZYME COMPOSITES HAVING CARRIERS DERIVATIZED WITH AN ORGANOTITANATE

[75] Inventor: Siu-Leung Lee, Painted Post, N.Y.

[73] Assignee: Ciba Corning Diagnostics Corp., Medfield, Mass.

[21] Appl. No.: 565,299

[22] Filed: Dec. 27, 1983

[51] Int. Cl.[4] .................... C12N 11/14; C12N 11/02; C12N 11/10; C12N 11/12

[52] U.S. Cl. .................................. 435/176; 435/177; 435/178; 435/179

[58] Field of Search ............... 435/177, 178, 179, 176

[56] References Cited

U.S. PATENT DOCUMENTS 3,519,538 7/1970 Messing et al. ............. 260/112.5 R
3,841,969 10/1974 Emery et al. .
4,267,273 5/1981 Smith ................................ 435/178

OTHER PUBLICATIONS

A. R. MacRae, "Lipase-Catalyzed Interesterification of Oils and Fats", JAOCS, vol. 60, No 2, Feb. 1983, p. 243A et. seq.

*Primary Examiner*—Esther M. Kepplinger
*Assistant Examiner*—Louanne C. Krawczewicz
*Attorney, Agent, or Firm*—B. D. Voyce

[57] ABSTRACT

The present invention relates to a novel immobilized enzyme composite. Suitable carriers such as controlled pore glasses or paper are coupled to various enzymes by derivatizing the carrier with an organotitanate. These composites are particularly suited for enzymatic reactions which prefer a non-aqueous, hydrophobic environment.

12 Claims, No Drawings

IMMOBILIZED ENZYME COMPOSITES HAVING CARRIERS DERIVATIZED WITH AN ORGANOTITANATE

TECHNICAL FIELD

The present invention relates to a novel immobilized enzyme composite. Suitable carriers such as controlled pore glasses or paper are coupled to various enzymes by derivatizing the carrier with an organotitanate. These composites are particularly suited for enzymatic reactions which prefer a non-aqueous, hydrophobic environment.

BACKGROUND ART

The formation of an organo-metallic compound involving titanium in an immobilized enzyme composite is disclosed in U.S. Pat. No. 3,841,969, issued to Emery et al. A polysaccharide carrier is reacted with a titanium salt, such as $TiCl_4$ or $Ti_2(SO_4)_3$, to form an organo-metallic derivative of the polysaccharide. Suitable carrier materials are sawdust, wood chips, paper, and cotton wool.

An enzyme is attached to the organo-metallic derivatized polysaccharide by reacting the two in the presence of a buffer. Suitable enzymes include amylglucosidase, glucose oxidase, invertase, trypsin, alpha amylase, glucose isomerase, pronase, catalase, lactate dehydrogenase, and urease.

In a recent article "Lipase-Catalyzed Interesterification of Oils and Fats", A. R. MacRae, JAOCS, vol. 60, no. 2, February 1983, p 243A et. seq., the use of an immobilized composite in a non-aqueous environment is disclosed. The MacRae composite was a lipase absorbed onto alumina particles. In order to be active the composite had to be hydrated in a 10% aqueous solution prior to use.

DISCLOSURE OF THE INVENTION

The present invention relates to a novel immobilized enzyme composite product and process that uses an alkoxy organotitanate to bind an enzyme to an insoluble carrier.

For the purpose of this disclosure, organotitanates include compounds of the following general formula:

$(R_1O)\cdot Ti\cdot (OXR_2Y)_3$ $R_1$ represents the aliphatic part of a monoalkoxy group, e.g. isopropyl. $R_2$ signifies either an aliphatic or an aromatic radical, e.g. isoheptadecyl, phenyl, and ethylene. X symbolizes a binding group which connects titanium to $R_2$, e.g. carboxyl, phenyl, sulfonyl, and pyrophosphate linkage. Y stands for a second functional group, e.g. methacrylic, acrylic, amino, mercapto, hydroxyl, and hydrogen groups. Either $R_2$ or Y can be absent, but not both. Bulletin No. KR-0278-7 Revision No. 2 from Kenrich Petrochemicals, Inc. of Bayonne, N.J., USA describes many of these compounds.

Suitable carriers are insoluble materials to which the organotitanate can be bound. Examples are siliceous materials, controlled pore glasses, controlled pore ceramics, and polysaccharides, i.e., filter paper and wood chips. These are conventional materials having available oxide and hydroxyl groups and are used as carriers in other immobilized enzyme composites.

Finally, the last component of the composite, the enzyme, can also be chosen from a list of known materials. Hydrolytic, redox, and transferase enzymes are all suitable for the present composite. Specific enzymes include lipase, protease, glucose isomerase, and amylase.

The composite is assembled in a simple, two-step method. First, the carrier is derivitized with the organotitanate. In order to do this, one solubilizes the organotitanate. Then the carrier is immersed in the organotitanate solution for a time suitable to obtain the desired quantity of attachment. Preferable exposure times are 15 minutes to an hour. The second step is to load the enzyme onto the derivitized carrier. Typically, the enzyme is put into a buffer solution and the carrier immersed therein. However, the enzyme solution could just as easily be poured onto the carrier.

The present composites are particularly suited for reactions which require a hydrophobic reaction site, e.g. transesterifying oil and fats and esterification of fatty acids and alcohols. The organotitanate provides hydrophobic environment for the attached enzyme, thereby promoting the formation of hydrophobic esters such as lipid carboxylic esters. Synthetic jojoba oil substitutes such as erucyl erucate and behenyl analogs can be made easily with the present composite.

BEST MODE FOR CARRYING OUT THE INVENTION

Glass Carrier

In a preferred embodiment, the carrier was a controlled pore glass (CPG). One gram of CPG ($SiO_2$, 30/45 mesh, 400 Å average pore size) was mixed with 3 ml of dry isopropanol and 0.005 g of isopropyl, triisostearoyl titanate (ITT) (KR-TTS brand from Kenrich Petrochemical, Inc.). The mixture was vortexed, then allowed to stand for 30 minutes. The solvent was evaporated, and the 0.5% ITT-coated CPG composite precursor was washed and dried. An immobilized enzyme composite was made by adding ten microliters of *Rhizopus arrhizus* lipase (1875 units in sodium phosphate buffer, pH 6.0) to 100 mg of 0.5% ITT-CPG.

Transesterification

Example 1

Lipids were transesterified using composites made by the above method. A lipid solution having varying amounts of olive oil and $C^{14}$-Stearic acid in 5 ml of n-hexane were poured onto the composite. The lipid mixture was incubated on the composite at 25° C. for 66 and 72 hours.

The incorporation of $C^{14}$-Stearic acid into the olive oil triglycerides was analyzed by silica gel-thin layer chromatography. A solvent having petroleum ether, ethyl ether, and acetic acid in an 80-to-20-to-1 ratio separated the triglycerides which were visualized by iodine vapor. After the iodine evaporated, the triglyceride zone was placed in a 10 ml Scintilene ™ (Fisher Co.) cocktail and counted.

The incorporation was as follows:

| | | % Incorporation | |
|---|---|---|---|
| Stearic Acid | Olive Oil | 66 Hours | 72 Hours |
| 50 mg | 25 mg | 1.8 | 4.3 |
| 50 mg | 50 mg | 5.8 | 14.5 |
| 50 mg | 100 mg | 5.3 | 15.8 |
| 50 mg | 250 mg | 2.4 | 11.0 |

The incorporation of stearic acids as measured by the radioassay was later found to be lower than the actual incorporation due to absorption of material on the thin layer.

Example 2

A second experiment carried out in a column of immobilized lipase gave a yield of at least 64%. Fifty microliters of *Rhizopus arrhizus* lipase (209,000 units) were diluted to 200 μl with 0.1M sodium phosphate buffer (pH 6.0) and added to 2.0 g of 1% ITT-CPG. The immobilized enzyme was packed in a column (1 cm × 10 cm). A water saturated, n-hexane solution (50 ml) of 1.5 g each of olive oil and stearic acid was cycled through the column by a GE Minigear positive pump at 5.0 ml/min. The entire product was drained from the apparatus every 2 days and replaced with new substances in new solvent. The process was repeated for 14 days.

The products of each run were analyzed by HPLC. The formation of 1,3-distearyl-2-oleylglycerol was observed as a peak at Rt=6.06 (The HPLC column was a Radiopak C-18. A 36:64 acetone/acetonitrile solvent was eluted at 5 ml/min and detected by refractive index detector). The total integration of new triacylglycerols indicated an incorporation of at least 64%. The specificity of transesterification on the 1 and 3 positions was verified by hydrolysis of the transesterified products with porcine pancreas lipase (known to have 1,3 specificity). The radioactivity on the free fatty acids from the 1 and 3 positions as compared to the radioactivity on the 2-monoacylglycerol was greater than 99%.

The column was subject to recycling 14 times over one month with no apparent decrease in transesterification rate.

Paper Carrier

Another embodiment of the present composite used a paper carrier. The advantages were several. Paper was easily configured, relatively inexpensive, and easy to process both as a composite and as waste.

The paper composite was made and used like the glass ones. For example, a circle of 7 cm, ashless filter paper (Whatman 41) was dipped in a 1% ITT, n-hexane solution for 30 minutes and air-dried. Then a composite was made by spotting a 4.0 cm² section of the coated paper with a lipase solution (same as above). The composite was mixed with 1.0 mmole each of erucyl alcohol and erucic acid and 4.0 ml of n-hexane and incubated at ambient temperature for 48 hours. The yield of erucyl erucate ester was 40% in 4.5 hours and about 80–90% after 48 hours.

Having described the invention with particular reference to preferred form, it will be obvious to those skilled in the art to which the invention pertain, that, after understanding the invention, various changes and modifications may be made without departing from the spirit and scope of the invention as defined by the appended claims.

I claim:

1. An immobilized enzyme composite comprising:
   (a) an insoluble carrier;
   (b) an enzyme; and
   (c) an alkoxy organotitanate coupling compound which couples the enzyme to the carrier said alkoxy organotitanate having the following general formula: $(R_1O).Ti.(OXR_2Y)_3$ wherein $R_1$ represents the aliphatic part of a monoalkoxy group; $R_2$ is selected from the group consisting of isoheptadecyl, phenyl, and ethylene; X symbolizes a binding group which connects titanium to $R_2$, wherein X is selected from the group consisting of carboxyl, phenyl, sulfonyl, and pyrophosphate linkage; Y is selected from the group consisting of methacrylic, acrylic, amino, mercapto, hydroxyl, and hydrogen groups; and either $R_2$ or Y can be absent but not both.

2. The composite of claim 1 wherein the alkoxy organotitanate is isopropyl, triisostearoyl titanate.

3. The composite of claim 1 wherein the carrier is selected from the group consisting of ceramics, glasses and polysaccharides.

4. The composite of claim 3 wherein the carrier is selected from the group consisting of controlled pore glasses, controlled pore ceramics, and cellulosic material.

5. The composite of claim 1 wherein the enzyme is selected from the group consisting of hydrolytic, redox, and transferase enzymes.

6. The composite of claim 5 wherein the enzyme is lipase.

7. A method of immobilizing an enzyme comprising:
   (a) selecting an insoluble carrier;
   (b) coating the carrier with an alkoxy organotitanate coupling compound; said alkoxy organotitanate having the following general formula: $(R_1O).Ti.(OXR_2Y)_3$ wherein $R_1$ represents the aliphatic part of a monoalkoxy group; $R_2$ is selected from the group consisting of isoheptadecyl, phenyl, and ethylene; X symbolizes a binding group which connects titanium to $R_2$, wherein X is selected from the group consisting of carboxyl, phenyl, sulfonyl, and pyrophosphate linkage; Y is selected from the group consisting of methacrylic, acrylic, amino, mercapto, hydroxyl, and hydrogen groups; and either $R_2$ or Y can be absent but not both and
   (c) loading the enzyme onto the coated carrier.

8. The method of claim 7 wherein the alkoxy organotitanate is isopropyl, triisostearoyl titanate.

9. The method of claim 7 wherein the carrier is selected from the group consisting of ceramics, glasses and polysaccharides.

10. The method of claim 9 wherein the carrier is selected from the group consisting of controlled pore glasses, controlled pore ceramics, and cellulosic material.

11. The method of claim 7 wherein the enzyme is selected from the group consisting of hydrolytic, redox, and transferase enzymes.

12. The method of claim 11 wherein the enzyme is lipase.

* * * * *